United States Patent [19]

Horodysky et al.

[11] Patent Number: 4,537,692

[45] Date of Patent: Aug. 27, 1985

[54] ETHERDIAMINE BORATES AND LUBRICANTS CONTAINING SAME

[75] Inventors: Andrew G. Horodysky, Cherry Hill; Richard S. Herd, Woodbury, both of N.J.

[73] Assignee: Mobil Oil Corporation, New York, N.Y.

[21] Appl. No.: 646,199

[22] Filed: Aug. 31, 1984

Related U.S. Application Data

[62] Division of Ser. No. 535,133, Sep. 23, 1983.

[51] Int. Cl.$^3$ .......................... C10M 1/54; C10M 1/10
[52] U.S. Cl. ............................... 252/49.6; 252/32.7 E
[58] Field of Search .......................... 252/49.6, 32.7 E

[56] References Cited

U.S. PATENT DOCUMENTS

| | | | |
|---|---|---|---|
| 3,011,881 | 12/1961 | Emrick et al. | 44/76 |
| 3,257,442 | 6/1966 | Woods et al. | 44/72 |
| 4,406,802 | 9/1983 | Horodysky et al. | 44/76 |
| 4,478,732 | 10/1984 | Horodysky et al. | 252/49.6 |

*Primary Examiner*—Y. Harris-Smith
*Attorney, Agent, or Firm*—Alexander J. McKillop; Michael G. Gilman; Van D. Harrison, Jr.

[57] ABSTRACT

Borates of certain etherdiamines are provided. These compounds give excellent results when tested in lubricants as friction reducing antioxidants or antirust additives.

15 Claims, No Drawings

ETHERDIAMINE BORATES AND LUBRICANTS CONTAINING SAME

This is a divisional of copending application Ser. No. 535,133, filed on Sept. 23, 1983.

BACKGROUND OF THE INVENTION

1. Field of the Invention

The invention relates to lubricant compositions. More particularly, it relates to a group of etherdiamine borates and to their use in lubricants as multipurpose additives, i.e., as rust, friction, antioxidant and fuel consumption reducers. The invention is especially concerned with lubricating internal combustion engines.

2. Discussion of Related Art

As those skilled in this art know, additives impart special properties to lubricants. They may give the lubricants new properties or they may enhance properties already present. One property all lubricants must have is the reduction of rust on lubricated parts in contact.

Borated amides, borated alkanolamines, borated ureas, amine salts of boron acids, chlorinated amine-boron complexes and aromatic amine-boron mixtures have been used in the past as described in U.S. Pat. Nos. 3,449,362, 3,254,025, 2,999,064, 4,226,734, 3,076,835, 4,025,446, 3,014,870, 3,014,869 and 3,007,873. Related borated adducts of alkylamines and alkyldiamines are disclosed as lubricant friction reducers in U.S. Pat. No. 4,328,113. The alkyldiamine borates disclosed in U.S. Pat. No. 4,328,113 do not, however, possess significant antirust properties. The etherdiamine borates disclosed herein have been compared with alkyldiamine borates and found to possess far superior antirust properties. As a result, our etherdiamine borates described herein provide substantial antirust, friction reducing, oxidative and high temperature stability advantages unavailable in any of the prior art disclosures.

SUMMARY OF THE INVENTION

In accordance with the invention, there is provided a lubricant or liquid fuel composition comprising a major proportion of a lubricant or liquid fuel and a friction reducing, a fuel consumption reducing or an antioxidant amount of a reaction product made by reacting a boron compound with a N-hydrocarbyloxyhydrocarbylenediamine of the formula

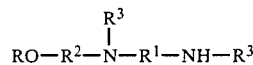

wherein R is a hydrocarbyl group containing 6 to 30 carbon atoms, $R^1$ and $R^2$ are $C_2$ to $C_3$ hydrocarbylene groups and $R^3$ is preferably hydrogen or a $C_1$ to $C_5$ hydrocarbyl group. It will be understood that "hydrocarbyl" and "hydrocarbylene" preferably refer to alkyl and alkylene groups, but the hydrocarbyl group may also be an aryl, alkaryl, aralkyl group, wherein the aryl portion contains 6 to 14 carbon atoms, or a cycloalkyl group.

The invention provides the compounds also.

DESCRIPTION OF THE SPECIFIC EMBODIMENTS

The borate-diamine products can be made by any method known to the art. In general, they can be made by reacting a diamine of the formula

wherein R, $R^1$, $R^2$ and $R^3$ are as hereinabove described with a boron compound.

The etherdiamines are generally available commercially. Those that are not can be made by (1) reacting an alcohol with a acrylonitrile and hydrogenating to form an ether amine and (2) reacting (1) with additional acrylonitrile and hydrogenating to form the etherdiamine.

The general reaction conditions are not critical. Reaction can take place between the diamine and the boron compound at a temperature of between about 80° C. and about 260° C., preferably about 110° C. to about 170° C. The reaction will usually be completed in from 2 to 10, but where the reactants demand it, up to 24 hours may be required for reaction completion.

Hydrocarbon solvents, or other inert solvents, may be used in the reaction. Included among the useful solvents are benzene, toluene and xylene. In general, any hydrocarbon solvent can be used in which the reactants are soluble and which can, if the products are soluble therein, be easily removed. Alcoholic solvents such as butanol, propanol or hexamethylene glycol can also be used as solvents.

Some of the useful diamines include hexoxypropyl-1-3-propylenediamine, heptoxypropyl-1,3-propylenediamine, octoxypropyl-1,3-propylenediamine, nonoxypropyl-1,3-propylenediamine, decoxypropyl-1,3-propylenediamine, dodecoxypropyl-1,3-propylenediamine, tridecoxypropyl-1,3-propylenediamine, isomeric tridecoxypropyl-1,3-propylenediamine, octadecoxy-1,3-propylenediamine, tetramethylnonyloxypropyl-1,3-propylenediamine and mixtures of two or more of these.

The useful boron compounds include the metaborates and low molecular weight trialkyl borates and boric acid. Preferred are the boric oxides and the boron compounds exemplified by the formula

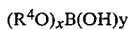

wherein $R^4$ is a $C_1$ to $C_6$ alkyl group, x is 0 to 3 and y is 0 to 3, their sum being 3. Molar ratios of etherdiamine to boron compound are selected so that at least 5 to 10% of the available nitrogen, and preferably 50-95% thereof, is borated. Up to a stoichiometric amount of borating species, or an excess of 25 to 50% over stoichiometric can be used, and is often preferred.

We believe that the nitrogens of the etherdiamine are borated to form N-B bonds, but we do not know their exact nature. While the reaction outlined is the usual one, other reactions may be occurring to give a uniquely complex product. Molar ratios of reactants, i.e., etherdiamine and boron compound, may be from about 4:1 to about 1:2, preferably about 2:1 to about 1:1.

An important feature of the invention is the ability of the additive to improve the resistance to oxidation of oleaginous materials such as lubricating oils, either a mineral oil or a synthetic oil, or mixtures thereof, or a grease in which any of the aforementioned oils are employed as a vehicle. In general, mineral oils, both paraffinic, naphthenic and mixtures thereof, employed as a lubricating oil or as the grease vehicle, may be of any suitable lubricating viscosity range, as for example, from about 45 SSR at 100° F. to about 6000 SSU at 100° F., and preferably from about 50 to about 250 SSR at 210° F. These oils may have viscosity indexes ranging to about 100 or higher. Viscosity indexes from about 70 to about 95 are preferred. The average molecular weights of these oils may range from about 250 to about 800. Where the lubricant is to be employed in the form of a grease, the lubricating oil is generally employed in an amount sufficient to balance the total grease composition, after accounting for the desired quantity of the thickening agent, and other additive components to be included in the grease formulation. A wide variety of materials may be employed as thickening or gelling agents. These may include any of the conventional metal salts or soaps, such as calcium, or lithium stearates or hydroxystearates, which are dispersed in the lubricating vehicle in grease-forming quantities in an amount to impart to the resulting grease composition the desired consistency. Other thickening agents that may be employed in the grease formulation may comprise the non-soap thickeners, such as surface-modified clays and silicas, aryl ureas, calcium complexes and similar materials. In general, grease thickeners may be employed which do not melt and dissolve when used at the required temperature within a particular environment; however, in all other respects, any material which is normally employed for thickening or gelling hydrocarbon fluids for forming grease can be used in preparing the aforementioned improved grease in accordance with the present invention.

In instances where synthetic oils, or synthetic oils employed as the vehicle for the grease, are desired in preference to mineral oils, or in preference to mixtures of mineral and synthetic oils, various synthetic oils may be successfully utilized. Typical synthetic vehicles include polyisobutylenes, polybutenes, hydrogenated polydecenes, polypropylene glycol, polyethylene glycol, trimethylol propane esters, neopentyl and pentaerythritol esters, di(2-ethylhexyl)sebacate, di(2-ethylhexyl)adipate, dibutyl phthalate, fluorocarbons, silicate esters, silanes, esters of phosphorus-containing acids, liquid ureas, ferrocene derivatives, hydrogenated synthetic oils, chain-type polyphenyls, siloxanes and silicones (polysiloxanes) and alkyl-substituted diphenyl ethers typified by a butyl-substituted bis(p-phenoxy phenyl)ether, phenoxy phenylethers.

It is to be understood that the compositions contemplated herein can also contain other materials. For example, other corrosion inhibitors, extreme pressure agents, viscosity index improvers, coantioxidants, antiwear agents and the like can be used. These include, but are not limited to, phenates, sulfonates, succinimides, zinc dialkyl or diaryl dithiophosphates, and the like. These materials do not detract from the value of the compositions of this invention.

Mineral oil heat exchange fluids particularly contemplated in accordance with the present invention have the following characteristics: high thermal stability, high initial boiling point, low viscosity, high heat-carrying ability and low corrosion tendency.

Further, the transmission fluids of consequence to the present invention are blends of highly refined petroleum base oils combined with VI improvers, detergents, defoamants and special additives to provide controlled-friction or lubricity characteristics. Varied transmission design concepts have led to the need for fluids with markedly different frictional characteristics, so that a single fluid cannot satisfy all requirements. The fluids intended for use in passenger car and light-duty truck automatic transmissions are defined in the ASTM Research Report D-2; RR 1005 on "Automatic Transmission Fluid/Power Transmission Fluid Property and Performance Definitions. Specifications for low-temperature and aircraft fluids are defined in U.S. Government Specification MIL-H-5606A.

In addition, the oxidation and corrosion resistance of functional fluids such as hydraulic fluids can be improved by the adducts of the present invention.

The products of this invention can also be employed in liquid hydrocarbon fuels, alcohol fuels or mixtures thereof, including mixtures of hydrocarbons, mixtures of alcohols and mixtures of hydrocarbon and alcohol fuels. About 25 pounds to about 500 pounds or preferably about 50 to 100 pounds of etherdiamine amide per thousand barrels of fuel for internal combustion engines may be used. Liquid hydrocarbon fuels include gasoline, fuel oils and diesel oils. Methyl and ethyl alcohols are examples of alcohol fuels.

In general, the reaction products of the present invention may be employed in any amount which is effective for imparting the desired degree of friction reduction or antioxidant activity. In these applications, the product is effectively employed in amounts from about 0.1% to about 10% by weight, and preferably from about 1% to about 5% of the total weight of the composition.

The following Examples will present illustrations of the invention. They are illustrative only, and are not meant to limit the invention.

EXAMPLE 1

Partially Borated
N-Tetramethylnonyloxypropyl-1,3-propylenediamine

N-tetramethylnonyloxypropyl-1,3-propylenediamines (commercially available as Duomeen EA-13 from Armak Co. and derived from an isomeric tridecyl alcohol consisting primarily of tetramethylnonyl alcohol) had an average molecular weight of approximately 315. Approximately 255 g of this diamine, about 100 g of toluene and 9 g of boric acid were changed to a 1 liter glass reactor fitted with an agitator, heater, and Dean-Stark tube with condenser. The reactor contents were heated up to about 155° C. with agitation using a slow nitrogen purge of the vapor space. The reactor contents were held at about 155° C. for four additional hours until water evolution via azeotropic distillation ceased. The solvent was removed by vacuum distillation at 150° C. and the partially borated etherdiamine was filtered hot through diatomaceous earth.

EXAMPLE 2

Borated
N-Tetramethylnonyloxypropyl-1,3-propylenediamine

Approximately 324.5 g of N-tetramethylnonyloxypropyl-1,3-propylenediamine as described in Example 1, about 100 g of toluene and about 23 g of boric acid were charged to a 1 liter glass reactor fitted with an agitator, heater and Dean-Stark tube with condenser. The reactor contents were heated up to about 155° C. with agitation using a slow nitrogen purge of the vapor space. The reactor contents were held at about 155° C. until water evolution via azeotropic distillation ceased.

The solvent was removed by vacuum distillation at 150° C. and the borated ether diamine was filtered hot through diatomaceous earth.

COMPARATIVE EXAMPLE 3

Partially Borated N-Oleyl-1,3-Propylenediamine

Approximately 276 g of N-oleyl-1,3-propylenediamine (commercially available as Duomeen 0 from Armak Co.), 35 g of toluene and 10 g of boric acid were changed to a 1 liter glass reactor fitted with an agitator, heater and Dean-Stark tube with condenser. The reactor contents were heated up to 150° C. with agitation using a slow nitrogen purge of the vapor space. The reactor contents were held at 150° C. for 4.5 hours until water evolution stopped. The solvent was removed by vacuum distillation and the partially borated alkyldiamine was filtered hot through diatomaceous earth.

EVALUATION OF COMPOUNDS

The products of the Examples were formulated at the 2% wt. level into a fully formulated lithium soap grease containing amine antioxidant, phenolic antioxidant, metallic dithiophosphate and sulfur-containing metal deactivator. The grease was made from a solvent naphthenic refined lubricating oil base stock, without any other added antirust additive. The grease was then evaluated for antirust properties using an extremely severe rust test performed with 5% synthetic sea water.

A standard test method (modified ASTM D1743) for corrosion preventive properties of lubricating grease is used. The method covers the determination of the corrosion preventive properties of greases using grease-lubricated tapered roller bearings stored under wet conditions. After cleaning, the bearing cup raceways are examined for evidence of corrosion.

TABLE 1

| Evaluation of Antirust Properties | | |
|---|---|---|
| Composition | Additive Conc., Wt. % | Rust Test Results* |
| Base Grease (lithium soap grease) | — | 3-10%, 3-15% |
| Example 1 plus grease | 2 | 1,2, 1,2+ |
| Example 2 plus grease | 2 | 1,2+ |
| Example 3 plus grease | 2 | 3-2%, 3-10% |

*A bearing cup raceway showing no corrosion is rated 1. No more than 3 spots of a size just sufficient to be visible to the naked eye is rated 2. More than 3 spots but less than 1% of the surface area is rated 2+. 1% or more of the surface area corroded is rated 3. (Note: the approximate percent of surface area corrosion is shown with a 3 rating.)

The antirust test results clearly show the antirust properties of the N-alkoxyalkylenediamine borates (Examples 1 and 2) to be clearly superior, even when compared to the N-alkylalkylenediamine borates (Example 3).

The products were also evaluated for high temperature and oxidative stability. In most cases improvements in oxidative stability were observed. Basically, the test lubricant is subjected to a stream of air which is bubbled through at a rate of 5 liters per hour at 325° F. for 40 hours. Present in the composition are samples of metals commonly used in engine construction, namely iron, copper, aluminum and lead. See U.S. Pat. No. 3,682,980 (incorporated herein by reference) for further details of the test. Improvement in percent viscosity) increase or control of neutralization number (or both) show effective control. As shown by the results of Table 2, antioxidant properties are exhibited by the compositions.

TABLE 2

| Catalytic Oxidation Test | | | | |
|---|---|---|---|---|
| Composition | Additive Conc. Wt. % | % Increase in Viscosity of Used Oil vs. New Oil @ 100° C. KV | Acid No. | Pb. Loss, mg |
| Base Oil 200" Solvent Paraffinic Neutral Mineral Lubricating Oil | — | 27 | 2.21 | 0.4 |
| Example 1 plus oil | 1 | 18 | 2.47 | 0.2 |
|  | 3 | 17 | 1.73 | 0.0 |
| Example 2 plus oil | 1 | 12 | 2.03 | 0.0 |
|  | 3 | 13 | 1.45 | 0.1 |

The compounds were evaluated in a Low Velocity Friction Apparatus (LVFA) in a fully formulated synthetic 5W-30 automotive engine oil containing an additive package including antioxidant, dispersant and detergent, and specifically including metallic phenates, sulfonates and dithiophosphates.

DESCRIPTION

The Low Velocity Friction Apparatus (LVFA) is used to measure the coefficient of friction of test lubricants under various loads, temperatures, and sliding speeds. The LVFA consists of a flat SEA 1020 steel surface (diameter 1.5 in.) which is attached to a drive shaft and rotated over a stationary, raised, narrow ringed SAE 1020 steel surface (area 0.08 in.$^2$. Both surfaces are submerged in the test lubricant. Friction between the steel surfaces is measured as a function of the sliding speed at a lubricant temperature of 250° F. The friction between the rubbing surfaces is measured using a torque arm-strain gauge system. The strain gauge output, which is calibrated to be equal to the coefficient of friction, is fed to the Y axis of an X-Y plotter. The speed signal from the tachometer-generator is fed to the X-axis. To minimize external friction, the piston is supported by an air bearing. The normal force loading the rubbing surfaces is regulated by air pressure on the bottom of the piston. The drive system consists of an infinitely variable-speed hydraulic transmission driven by a ½ HP electric motor. To vary the sliding speed, the output speed of the transmisson is regulated by a lever-cammotor arrangement.

PROCEDURE

The rubbing surfaces and 12–13 ml of test lubricants are placed on the LVFA. A 240 psi load is applied and the sliding speed is maintained at 40 fpm at ambient temperature for a few minutes. A plot for coefficients of friction ($U_k$) vs. speed were taken at 240, 300, 400, and 500 psi. Freshly polished steel specimens are used for each run. The surface of the steel is parallel ground to 4 to 8 microinches. The results in Table 3 refer to percent reduction in friction compared to the unmodified oil. That is, the formulation mentioned above was tested without the compound of this invention and this became the basis for comparison. The results were obtained at 250° F. and 500 psi.

As shown in Table 3, the borated alkoxyalkylenediamines exhibit unexpected friction reducing properties, considering the potent antirust characteristics.

TABLE 3

| | Evaluation of Friction Reducing Characteristics | |
|---|---|---|
| | Additive | % Change in Coeff. of Friction |
| Compositiom | Conc. Wt. % | 5 Ft./Min. | 30 Ft./Min. |
|---|---|---|---|
| Base Oil | — | 0 | 0 |
| Example 1 plus oil | 2 | 17 | 16 |
| Example 2 plus oil | 2 | 18 | 17 |
| | 1 | 14 | 13 |

The coefficients of friction were significantly reduced relative to the base oil. Significant reductions in the coefficients of friction were noted with the use of only 1% of Example 2 admixed into a fully formulated lubricant containing detergent/dispersant/inhibitor/viscosity index improving additive package. Lower concentrations of less than 1% are also expected to contribute significantly to reductions in friction.

We claim:

1. A lubricant composition comprising a major proportion of an oil lubricating viscosity and a minor antioxidant or antifriction amount of a product of reaction made by reacting a N-hydroxcarbyloxyhydrocarbyleneamine of the formula

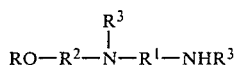

wherein R is a hydrocarbyl group containing 6 to 30 carbon atoms, $R^1$ and $R^2$ are hydrocarbylene groups containing 2 to 3 carbon atoms and $R^3$ is hydrogen or a $C_1$ to $C_5$ hydrocarbyl group with a boron compound.

2. The composition of claim 1 wherein in the product the hydrocarbyl group is an alkyl, aryl, alkaryl, aralkyl or cycloalkyl group.

3. The composition of claim 1 wherein in the hydrocarbylene group is an alkylene group.

4. The composition of claim 2 wherein in the hydrocarbyl group is hexyl, heptyl, octyl, nonyl, decyl, dodecyl, tridecyl, tetramethylnonyl or octadecyl.

5. The composition of claim 1 wherein in the boron compound boric oxide or has the formula $$(R^4O)_xB(OH)_y$$

wherein $R^4$ is a $C_1$ to $C_6$ alkyl group, x is 0 to 3 and y is 0 to 3, their sum being 3.

6. The composition of claim 5 wherein in the boron compound is boric acid.

7. The composition of claim 1 wherein in the diamine is N-tetramethylnonyloxypropyl-1,3-propylenediamine and the boron compound is boric acid.

8. The composition of claim 1 wherein the lubricant is (1) a mineral oil, (2) a synthetic oil or mixture of synthetic oils, (3) a mixture of a mineral oil and a synthetic oil or mixture of synthetic oils or (4) a grease of a mineral oil, a synthetic oil, a mixture of synthetic oils, or a mixture of mineral oil and synthetic oil.

9. The composition of claim 8 wherein the lubricant is a mineral oil.

10. The composition of claim 8 wherein the lubricant is a synthetic oil or mixture of synthetic oils.

11. The composition of claim 8 wherein the lubricant is a mixture as defined in (3) thereof.

12. The composition of claim 8 wherein the lubricant is a grease as defined in (4) thereof.

13. The composition of claim 12 wherein the grease is thickened with an alkali metal or alkaline earth metal soap of steric acid, hydroxystearic acid or the glycerides of such acids.

14. The composition of claim 8 wherein the lubricant additionally contains a member selected from the group consisting of metal phenates, metal sulfonates, succinamides, metal dialkyl phosphorodithioates, metal diaryl phosphorodithioates and mixtures of such additional members.

15. A method for decreasing fuel consumption of an internal combustion engine by lubricating the parts of said engine with a lubricant composition comprising a major portion of an oil of lubricating viscosity and a minor antioxidant or antifriction amount of a product of reaction made by reacting a N-hydrocarbyloxyhydrocarbylenediamine of the formula

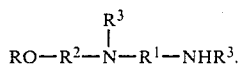

* * * * *